United States Patent [19]
Taheri

[11] Patent Number: 5,972,010
[45] Date of Patent: Oct. 26, 1999

[54] VEIN HARVESTING SYSTEM

[76] Inventor: Syde A. Taheri, 1275 Delaware Ave., Buffalo, N.Y. 14209

[21] Appl. No.: 09/079,087

[22] Filed: May 14, 1998

[51] Int. Cl.$^6$ .................................................. A61B 17/22
[52] U.S. Cl. .......................................... 606/159; 606/198
[58] Field of Search ................................... 606/108, 162, 606/198, 159

[56]  References Cited

U.S. PATENT DOCUMENTS

| | | | |
|---|---|---|---|
| 4,043,346 | 8/1977 | Mobley et al. .......................... | 606/198 |
| 5,235,966 | 8/1993 | Jamner ..................................... | 606/198 |

*Primary Examiner*—Michael Buiz
*Assistant Examiner*—Kevin Truong
*Attorney, Agent, or Firm*—Hodgson, Russ, Andrews, Woods & Goodyear LLP

[57]                ABSTRACT

The present invention comprises an apparatus and a method for harvesting veins. The apparatus includes an elongate member, a set of prongs disposed at the end of the member, a light carrying system for positioning the apparatus, and a triggering mechanism for opening and closing the prongs such that a vein can be dissected from surrounding tissue with minimal intrusiveness and minimal chance of damaging the surrounding tissue. Once the vein has been separated from the surrounding tissue by the apparatus, a vein dissector having an inflatable cover at the end is placed around the vein from the posterior and inflated and deflated to gently dissect the vein.

13 Claims, 4 Drawing Sheets

VEIN HARVESTING SYSTEM

FIELD OF THE INVENTION

The present invention relates to apparatus and methods for venous procurement, and more particularly to an apparatus for dissecting a vein and a method of harvesting a vein, with minimal intrusiveness and disruption of the surrounding tissue.

BACKGROUND OF THE INVENTION

A great number of cases of arterial bypass require venous procurement. The standard technique of vein harvesting requires a long incision from the groin to the ankle. This incision usually heals poorly and can be associated with a certain amount of infection and necrosis.

In order to avoid these problems less intrusive surgical procedures have been developed. However, the existing minimally intrusive techniques for vein harvesting require forceful forward movement of the harvesting instrument that results in damage to the surrounding tissue and that divides the venous collaterals, which causes late bleeding.

Accordingly, there is a need for a minimally intrusive vein harvesting system that reduces the likelihood of damage to the surrounding tissue and the venous collaterals.

SUMMARY OF THE INVENTION

The present invention solves the above described problem by providing a vein harvesting apparatus and a method of using the apparatus to harvest a saphenous vein, with minimal intrusiveness and with a reduction in the likelihood of damage to tissues surrounding the vein.

The present invention allows surgeons to dissect a vein from the surrounding tissue by opening and closing a set of prongs disposed at the end of an elongate member that is inserted underneath the skin in the area of the vein.

The apparatus of the present invention comprises an elongate member having a set of prongs attached at an end of the member. The prongs are actuated between a closed position and an open position by a triggering mechanism. The prongs are normally collapsed at the end to form a tip of decreasing cross-sectional area in order to make it easier to move the apparatus through the body. When the apparatus is placed in the correct position as determined by a scope, the prongs are opened and extended to dissect the vein from the surrounding tissue. The prongs are capable of being easily retracted once the vein has been captured by a separate instrument.

The method of the present invention comprises making an incision above the knee medially after the patient has been placed under general anesthesia and the leg has been prepared for surgery. Once the incision is made, the saphenous vein is identified through sharp dissection. Next, the vein harvesting apparatus is inserted under the skin and aimed toward the groin along the saphenous vein. A trigger mechanism is actuated which opens the prongs up to dissect the saphenous vein from the surrounding tissue. Once the vein has been dissected from the surrounding tissue by the prongs of the apparatus, a vein dissector is inserted posterior to the vein wall. The vein dissector has a curved end that curves in the shape of a "C." The curved end is covered with an inflatable plastic tube which provides for dissection of the vein posteriorly. The vein is dissected through gentle inflation and deflation of the vein dissector and then the branches of the vein are stapled and divided.

A similar procedure is performed distally toward the ankle, and then the saphenous vein is removed proximally and distally using staples.

Accordingly, it is an object of the present invention to provide an apparatus and a method for harvesting a vein.

The present invention provides several advantages including providing a minimally intrusive vein harvesting system. The apparatus and method do not require a long incision from the ankle to the groin. Also, the apparatus and method reduce the likelihood of damage to surrounding tissue.

Other objects, features, and advantages of the present invention will become apparent upon reading the following detailed description of embodiments of the invention, when taken in conjunction with the accompanying drawings and the appended claims.

DESCRIPTION OF THE PREFERRED EMBODIMENTS

Figure 1:
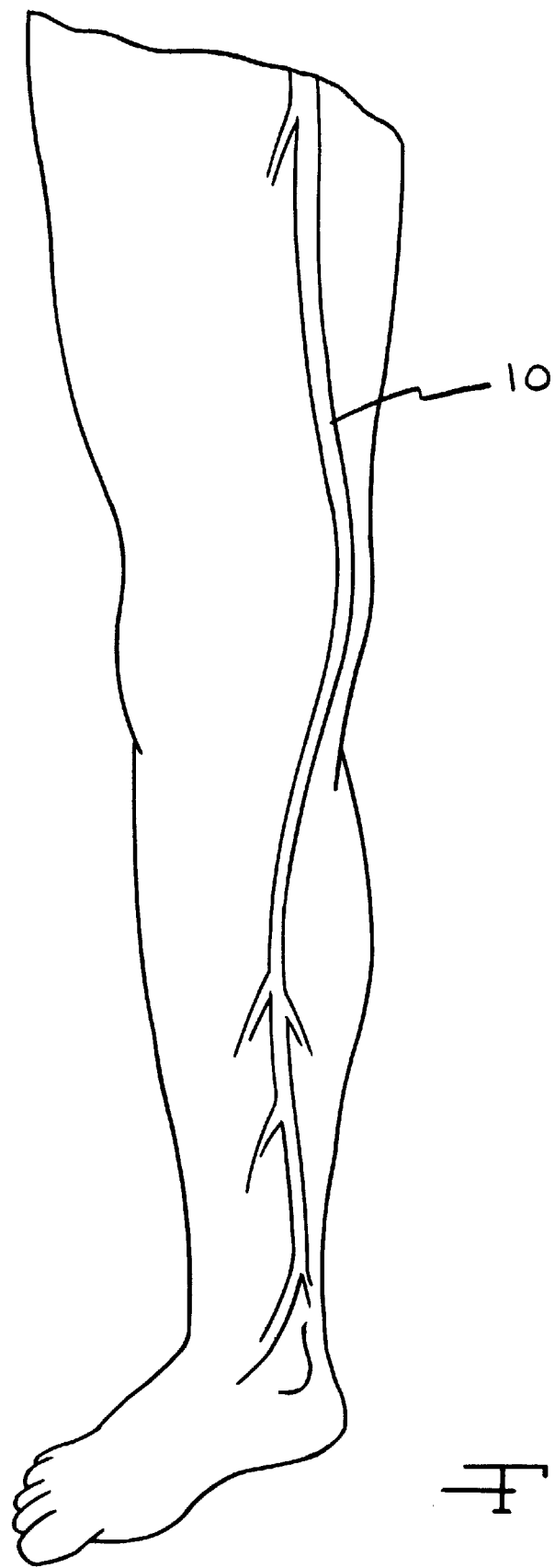
FIG. 1 is a perspective view of a normal saphenous vein which extends from the ankle to the groin.

In FIG. 1, a normal long saphenous vein 10 is shown as it extends from the ankle to the groin. The term saphenous vein refers to the two chief superficial veins of the leg. The internal saphenous vein or long saphenous vein originates in the foot and passes up the medial side of the leg and through the saphenous opening to join the femoral vein. The external saphenous vein or short saphenous vein originates in the foot and passes up the back of the leg to join the popliteal vein at the knee. The present invention is explained with reference to the long saphenous vein.

Figure 2:
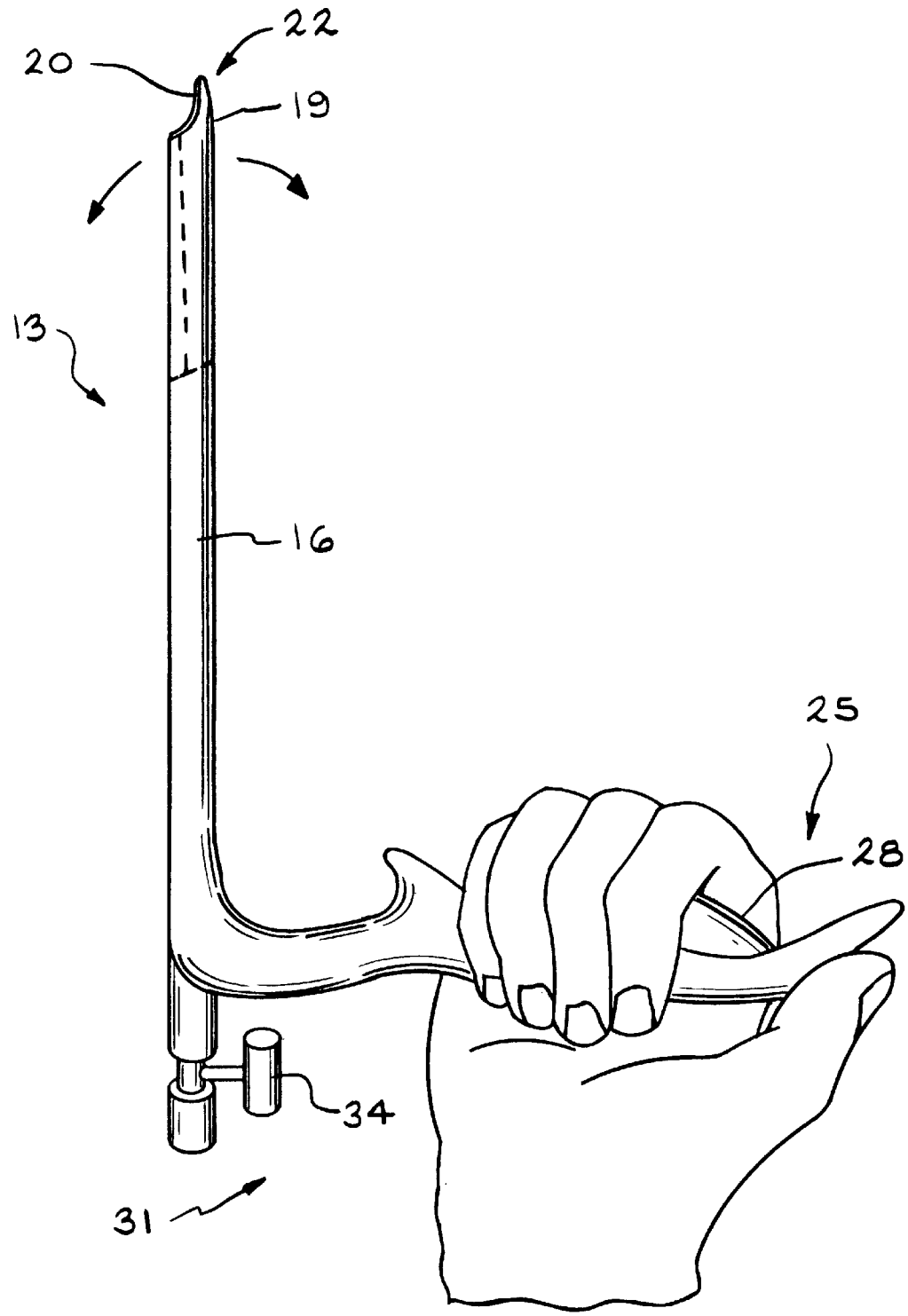
FIG. 2 is a perspective view of the vein harvesting apparatus of the present invention in the prong closed position.

In FIG. 2, a vein harvesting apparatus 13 comprises an elongate member 16. The elongate member 16 is preferably constructed of a plastic material which may be manufactured in numerous ways including injection molding, vacuum molding or the like. The member 16 is preferably L-shaped because the member 16 has to extend both underneath the skin of the patient and outside the patient for manual control of the apparatus 13 by the surgeon. A lumen (not shown) is provided along the length of the long leg of the L-shaped member 16 for passage of instruments such as forcepts and the like.

A set of collapsible prongs 19 is attached to a first end 22 of the member 16. The number of prongs 19 is variable, however different numbers and combinations of prongs 19 may be used. The important criteria being the ability of the prongs to collapse into a minimally intrusive end and the ability to move the surrounding tissue away from the vein 10.

The prongs 19 are normally closed or collapsed such that they form a tip 20 having a decreasing cross-sectional area compared to the member 16. In this manner the tip 20 of the apparatus 13 provides a minimal profile to reduce the likelihood of damage to tissue surrounding the vein 10. The prongs 19 are actuated between a closed position and an open position (best shown in FIG. 3) by a triggering mechanism 25. The triggering mechanism 25 causes the prongs 19 to move between a closed, collapsed position to an open, extended position preferably through a manual pneumatic system. Manual compression of an air bladder 28 causes movement of air from inside the bladder 28 to the end of the member 16 through a tube (not shown) inside the member 16. The air passage tube is preferably other than the previously described lumen providing passage of tools through the long leg of the member 16. The air pressure created at the end of the tube causes mechanical movement of the prongs 19 which pivot into the open position. Pneumatic systems such as this system are well known to those skilled in the art as well as other mechanical or electromechanical devices for opening and closing the prongs such as hydraulic, electrical, or electromagnetic systems and the like.

A light carrying system 31 comprising a light source (not shown) and a scope 34 is disposed along the elongate member 16. Once the apparatus 13 is inserted underneath the skin, the light carrying system 31 enables the surgeon to visualize the dissection of the saphenous vein 10. The light source illuminates the area inside the body around the end of the apparatus 13 and the scope 34 provides images of this area to the surgeon.

Figure 3:
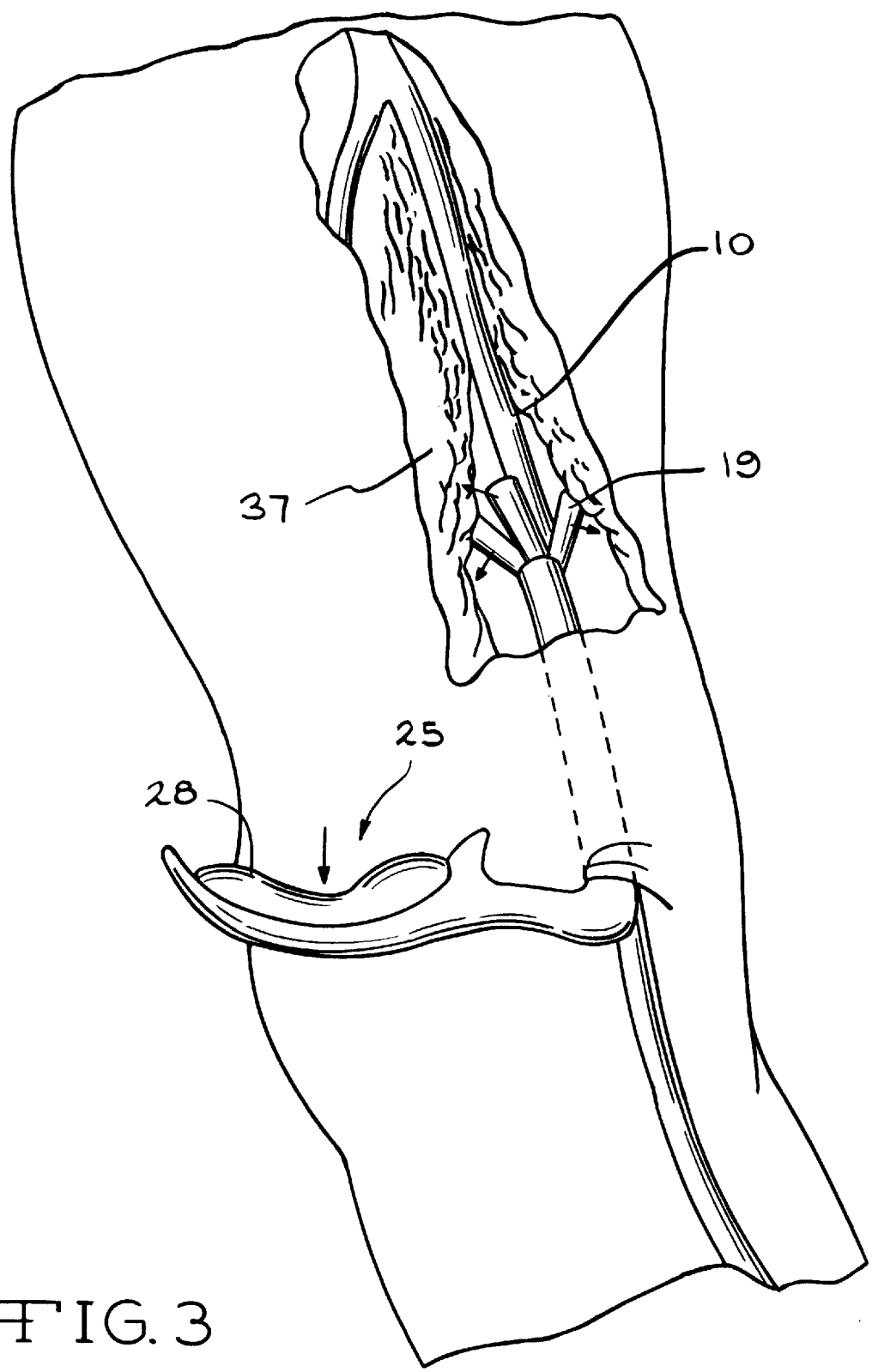
FIG. 3 is a perspective view of the vein harvesting apparatus of the present invention inserted under the skin and having the prongs in the open position to dissect the saphenous vein from the surrounding tissue.

In FIG. 3 the apparatus 13 is inserted underneath the skin and aimed at the groin. The apparatus 13 is placed in the desired position along the saphenous vein 10 through visualization by the light carrying system 31. As indicated by the arrow, the prongs 19 are deployed by operation of the triggering mechanism 25 through compression of the air bladder 28. The prongs 19 extend outwardly in all directions when deployed into the open position. In this manner, the prongs 19 are dissecting the saphenous vein 10 from the surrounding tissue 37.

Figure 4:
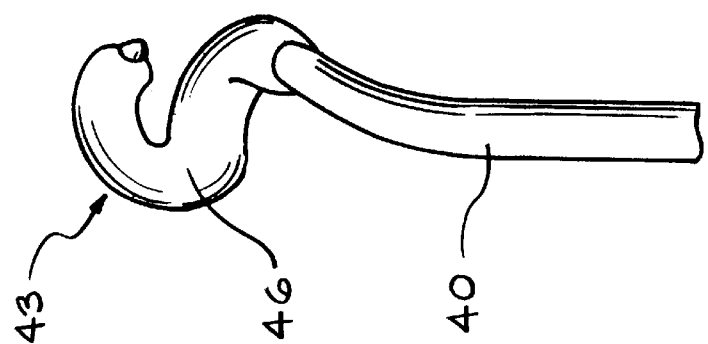
FIG. 4 is a perspective view of the vein dissector of the present invention with the inflatable cover deflated.

Turning to FIG. 4, a dissector 40 has a curved end 43 that is generally curved into a "C" shape. The curved end 43 is enclosed by an inflatable cover 46. The cover 46 is preferably constructed of a plastic material capable of forming an air tight membrane. The cover 46 is connected to an air line 49 having flow control (not shown) for controlling inflation and deflation.

Figure 5:
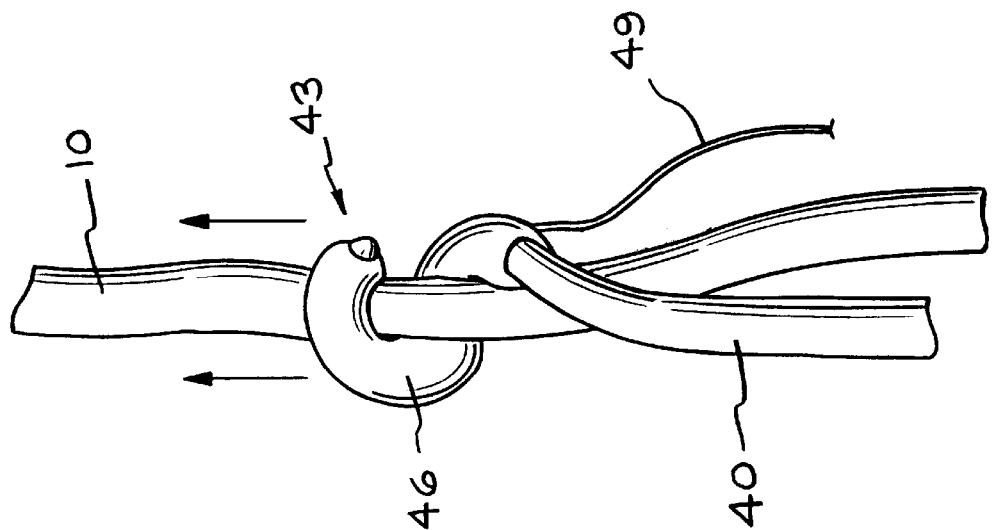
FIG. 5 is a perspective view of the vein dissector of the present invention with the inflatable cover inflated and wrapped around a vein for dissection.

In FIG. 5, the inflatable cover 46 is inflated and wrapped around a saphenous vein 10. The dissector 40 is designed to be inserted posterior to the wall of vein 10 and the cover is gently inflated and deflated in order to dissect the saphenous vein 10 from the surrounding tissue 37 without causing damage.

The apparatus 13 is used in the following manner to harvest a saphenous vein 10. An incision is made above the knee medially. The saphenous vein 10 is identified through sharp dissection. The vein harvesting apparatus 13 is then inserted under the skin and aimed toward the groin. Once the desired location of the apparatus 13 is found through use of the light carrying system 31, the prongs 19 at the end of the vein harvesting apparatus 13 are actuated by the triggering mechanism 25 to dissect the saphenous vein 10 from the surrounding tissue 37.

Once the saphenous vein 10 has been dissected from the surrounding tissue 37, the dissector 40 is inserted posterior to the wall of the saphenous vein and the inflatable cover 46 is manipulated to separate the saphenous vein 10 from the surrounding tissue 37. Finally, the branches of the saphenous vein 10 are stapled and divided.

After the branches of the vein 10 are stapled and divided a similar procedure is performed at the ankle. First, an incision is made below the knee medially. Next, the saphenous vein is identified by sharp dissection. The vein harvesting apparatus 13 is then inserted under the skin and aimed toward the ankle. Once the apparatus 13 is positioned through use of the light carrying system 31, the prongs 19 are actuated to dissect the vein 10 from the surrounding tissue 37. The dissector 40 is then moved posterior to the wall of the saphenous vein 10. The saphenous vein 10 is then separated from the surrounding tissue by manipulation of the inflatable cover 46 of the dissector 40. Next, the branches of the saphenous vein 10 are stapled and divided, and finally the saphenous vein 10 is removed with staples.

It is contemplated by the scope of the present invention that the view harvesting apparatus 13 is also useful for retrieval of lymphoid tissue and associated lymphatic vessels. For example, the present harvesting system is adaptable for removal of lymphoid tissue from the medistinoal and the retroperitoneal spaces.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A tissue harvesting apparatus, comprising:
   a) an elongate member having a side wall extending along a longitudinal axis to a first end and a second end, wherein the side wall of the elongate member extends partially about the longitudinal axis without completely surrounding the axis to provide an opening extending to the first and second ends, generally parallel to the longitudinal axis;
   b) a plurality of prongs pivotably connected to the side wall of the elongate member at the first end, wherein the prongs are capable of moving between an open and a closed configuration; and
   c) a triggering mechanism disposed at the second end of the elongate member and operatively associated with the prongs such that manipulation of the triggering mechanism causes the prongs to move between the open configuration and the closed configuration.

2. The apparatus of claim 1, wherein the closed configuration comprises the prongs converging along the longitudinal axis defined by the elongate member.

3. The apparatus of claim 2, wherein the open configuration comprises each of the plurality of prongs extending away from the axis in opposite directions.

4. The apparatus of claim 1, wherein the prongs are collapsible into a minimally intrusive configuration.

5. The apparatus of claim 1, wherein the second end of the elongate member is connected to a triggering mechanism.

6. The apparatus of claim 1, further comprising a light carrying system disposed along the elongate member, the system having a light source for illuminating an area surrounding the first end of the elongate member and having a scope at the second end of the elongate member, the scope being operatively associated with the light source such that the area surrounding the first end of the elongate member is capable of being viewed.

7. The apparatus of claim 1, wherein the triggering mechanism comprises an air bladder operatively associated with the prongs such that air pressure causes the prongs to move between the closed configuration and the open configuration.

8. The apparatus of claim 1, wherein the tissue is a vein.

9. The apparatus of claim 1, wherein the tissue is lymphoid tissue.

10. The apparatus of claim 9, wherein the lymphoid tissue is removed from either a medistinoad or a retroperitoneal space.

11. The apparatus of claim 1 wherein the side wall of the elongate member is curved about the longitudinal axis.

12. A tissue harvesting apparatus, comprising:
   a) an elongate member having a first end and a second end;
   b) a plurality of prongs disposed at the first end of the elongate member and capable of moving between an open configuration and a closed configuration;
   c) a triggering mechanism disposed at the second end of the elongate member and operatively associated with the prongs such that manipulation of the triggering mechanism causes the prongs to move between the open and the closed configurations; and
   d) a light carrying system disposed along the elongate member, the system having a light source for illuminating an area surrounding the first end of the elongate member and having a scope at the second end of the elongate member, the scope being operatively associated with the light source such that the area surrounding the first end of the elongate member is capable of being viewed.

13. A tissue harvesting apparatus, comprising:
   a) an elongate member having a first end and a second end;
   b) a plurality of prongs disposed at the first end of the elongate member and capable of moving between an open configuration and a closed configuration;
   c) a triggering mechanism disposed at the second end of the elongate member and operatively associated with the prongs such that manipulation of the triggering mechanism causes the prongs to move between the open and the closed configurations; and
   d) an air bladder comprising the triggering mechanism and operatively associated with the prongs such that air pressure from actuation of the air bladder causes the prongs to move between the closed configuration and the open configuration.

\* \* \* \* \*